(12) United States Patent
Schneider

(10) Patent No.: US 9,295,505 B2
(45) Date of Patent: Mar. 29, 2016

(54) BONE PLATE

(71) Applicant: DePuy Synthes Products, Inc., Raynham, MA (US)

(72) Inventor: Rolf Schneider, Tolochenaz (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/505,625

(22) Filed: Oct. 3, 2014

(65) Prior Publication Data

US 2015/0018889 A1 Jan. 15, 2015

Related U.S. Application Data

(63) Continuation of application No. 13/795,596, filed on Mar. 12, 2013, now Pat. No. 8,876,873, which is a continuation of application No. 13/713,626, filed on Dec. 13, 2012, now Pat. No. 8,845,698, which is a continuation of application No. 11/361,942, filed on Feb. 24, 2006, now Pat. No. 8,343,196, which is a continuation of application No. PCT/CH03/00577, filed on Aug. 26, 2003.

(51) Int. Cl.
*A61B 17/80* (2006.01)
*A61L 27/18* (2006.01)
*A61L 31/06* (2006.01)

(52) U.S. Cl.
CPC ............ *A61B 17/8033* (2013.01); *A61B 17/80* (2013.01); *A61B 17/8052* (2013.01); *A61B 17/8057* (2013.01); *A61L 27/18* (2013.01); *A61L 31/06* (2013.01); *A61L 2430/02* (2013.01)

(58) Field of Classification Search
CPC ........... A61B 17/8033; A61B 17/8082; A61L 27/18; A61L 31/06
USPC ...................................... 606/70, 71, 280–331
See application file for complete search history.

(56) References Cited

U.S. PATENT DOCUMENTS

| | | |
|---|---|---|
| 1,203,546 A | 10/1916 | Parsons |
| 2,228,584 A | 1/1941 | Place |
| 2,443,363 A | 6/1948 | Townsend et al. |
| 2,477,430 A | 7/1949 | Swanstrom |
| 2,846,701 A | 8/1958 | Bedford |

(Continued)

FOREIGN PATENT DOCUMENTS

| | | |
|---|---|---|
| CA | 1112803 | 11/1981 |
| CA | 2536960 | 3/2005 |

(Continued)

OTHER PUBLICATIONS

"Cone Drive History and Double Enveloping Technology", http://conedrive.com/history/html, accessed Apr. 20, 2006, 9 pages.

(Continued)

*Primary Examiner* — Christopher Beccia
(74) *Attorney, Agent, or Firm* — Baker & Hostetler LLP

(57) ABSTRACT

A bone plate has an underside on the side of the bone, an upper side and a plurality of holes in the plate connecting the underside with the upper side, with a central hole axis. At least one of these holes in the plate has an internal jacket surface that tapers towards the underside, while the internal jacket surface has $N \geq 3$ recesses which extend radially away from the axis of the hole.

38 Claims, 3 Drawing Sheets

(56) References Cited

U.S. PATENT DOCUMENTS

| | | |
|---|---|---|
| 3,229,743 A | 1/1966 | Derby |
| 3,263,949 A | 8/1966 | Conrad |
| 3,314,326 A | 4/1967 | Bedford |
| 3,364,807 A | 1/1968 | Holton |
| 3,388,732 A | 6/1968 | Holton |
| 3,463,148 A | 8/1969 | Treace |
| 3,551,389 A | 12/1970 | Prince et al. |
| 3,552,389 A | 1/1971 | Allgower et al. |
| 3,630,261 A | 12/1971 | Gley |
| 3,668,972 A | 6/1972 | Allgower et al. |
| 3,695,618 A | 10/1972 | Woolley et al. |
| 3,716,050 A | 2/1973 | Johnston |
| 3,741,205 A | 6/1973 | Markolf et al. |
| 3,744,488 A | 7/1973 | Cox |
| 3,779,240 A | 12/1973 | Kondo |
| 3,877,339 A | 4/1975 | Muenchinger |
| RE28,841 E | 6/1976 | Allgower et al. |
| 3,967,049 A | 6/1976 | Brandt |
| 3,996,834 A | 12/1976 | Reynolds |
| 4,029,091 A | 6/1977 | Von Bezold et al. |
| 4,175,555 A | 11/1979 | Herbert |
| 4,219,015 A | 8/1980 | Steinemann |
| 4,263,904 A | 4/1981 | Judet |
| 4,304,039 A | 12/1981 | Asmus |
| 4,338,926 A | 7/1982 | Kummer et al. |
| 4,355,198 A | 10/1982 | Gartland, Jr. |
| 4,408,601 A | 10/1983 | Wenk |
| 4,429,690 A | 2/1984 | Angelino-Pievani |
| RE31,628 E | 7/1984 | Allgower et al. |
| 4,484,570 A | 11/1984 | Sutter et al. |
| 4,491,317 A | 1/1985 | Bansal |
| 4,493,317 A | 1/1985 | Klaue |
| 4,513,744 A | 4/1985 | Klaue |
| 4,565,193 A | 1/1986 | Streli |
| 4,580,225 A | 4/1986 | Thompson |
| 4,612,923 A | 9/1986 | Kronenthal |
| 4,630,985 A | 12/1986 | Simons |
| 4,651,724 A | 3/1987 | Berentey et al. |
| 4,683,878 A | 8/1987 | Carter |
| 4,717,613 A | 1/1988 | Ottaviano |
| 4,776,329 A | 10/1988 | Treharne |
| 4,781,183 A | 11/1988 | Casey et al. |
| 4,794,918 A | 1/1989 | Wolter |
| 4,838,252 A | 6/1989 | Klaue |
| 4,858,601 A | 8/1989 | Glisson |
| 4,867,144 A | 9/1989 | Karas et al. |
| 4,927,421 A | 5/1990 | Goble et al. |
| 4,957,497 A | 9/1990 | Hoogland et al. |
| 4,988,350 A | 1/1991 | Herzberg |
| 5,002,544 A | 3/1991 | Klaue et al. |
| 5,006,120 A | 4/1991 | Carter |
| 5,027,904 A | 7/1991 | Miller et al. |
| 5,039,265 A | 8/1991 | Rath et al. |
| 5,041,113 A | 8/1991 | Biedermann et al. |
| 5,041,114 A | 8/1991 | Chapman et al. |
| 5,053,036 A | 10/1991 | Perren et al. |
| 5,085,660 A | 2/1992 | Lin |
| 5,108,399 A | 4/1992 | Eitenmuller et al. |
| 5,129,901 A | 7/1992 | Decoste |
| 5,147,361 A | 9/1992 | Ojima et al. |
| 5,151,103 A | 9/1992 | Tepic et al. |
| 5,190,544 A | 3/1993 | Chapman et al. |
| 5,197,966 A | 3/1993 | Sommerkammp |
| 5,261,910 A | 11/1993 | Warden et al. |
| 5,269,784 A | 12/1993 | Mast |
| 5,275,601 A | 1/1994 | Gogolewski et al. |
| 5,304,180 A | 4/1994 | Slocum |
| 5,306,275 A | 4/1994 | Bryan |
| 5,324,290 A | 6/1994 | Zdeblick et al. |
| 5,336,224 A | 8/1994 | Selman |
| 5,360,448 A | 11/1994 | Thramann |
| 5,364,398 A | 11/1994 | Chapman et al. |
| 5,364,399 A | 11/1994 | Lowery et al. |
| 5,403,136 A | 4/1995 | Mathys |
| 5,429,641 A | 7/1995 | Gotfried |
| 5,514,138 A | 5/1996 | McCarthy |
| 5,534,032 A | 7/1996 | Hodorek |
| 5,558,674 A | 9/1996 | Heggeness et al. |
| 5,571,198 A | 11/1996 | Drucker et al. |
| 5,591,168 A | 1/1997 | Judet et al. |
| 5,601,551 A | 2/1997 | Taylor et al. |
| 5,601,553 A | 2/1997 | Trebing et al. |
| 5,607,426 A | 3/1997 | Ralph et al. |
| 5,607,428 A | 3/1997 | Lin |
| 5,620,445 A | 4/1997 | Brosnahan et al. |
| 5,674,222 A | 10/1997 | Berger et al. |
| 5,702,399 A | 12/1997 | Kilpela et al. |
| 5,709,686 A | 1/1998 | Talos et al. |
| 5,741,258 A | 4/1998 | Klaue et al. |
| 5,749,872 A | 5/1998 | Kyle et al. |
| 5,772,662 A | 6/1998 | Chapman et al. |
| 5,785,713 A | 7/1998 | Jobe |
| 5,810,823 A | 9/1998 | Klaue et al. |
| 5,938,664 A | 8/1999 | Winquist et al. |
| 5,954,722 A | 9/1999 | Bono |
| 5,961,524 A | 10/1999 | Crombie |
| 5,968,047 A | 10/1999 | Reed |
| 5,976,141 A | 11/1999 | Haag |
| 5,999,940 A | 12/1999 | Ranger |
| 6,001,099 A | 12/1999 | Huebner |
| 6,022,352 A | 2/2000 | Vandewalle |
| 6,030,162 A | 2/2000 | Huebner |
| 6,030,389 A | 2/2000 | Wagner et al. |
| 6,096,040 A | 8/2000 | Esser |
| 6,129,730 A | 10/2000 | Bono et al. |
| 6,152,927 A | 11/2000 | Farris et al. |
| 6,183,475 B1 | 2/2001 | Lester et al. |
| 6,206,881 B1 | 3/2001 | Frigg et al. |
| 6,228,085 B1 | 5/2001 | Theken et al. |
| 6,261,291 B1 | 7/2001 | Talaber et al. |
| 6,306,136 B1 | 10/2001 | Baccelli |
| 6,322,562 B1 | 11/2001 | Wolter |
| 6,342,055 B1 | 1/2002 | Eisermann et al. |
| 6,348,052 B1 | 2/2002 | Sammarco |
| 6,364,882 B1 | 4/2002 | Orbay |
| 6,423,064 B1 | 7/2002 | Kluger |
| 6,440,135 B2 | 8/2002 | Orbay et al. |
| 6,454,769 B2 | 9/2002 | Wagner et al. |
| 6,454,770 B2 | 9/2002 | Klaue |
| 6,468,278 B1 | 10/2002 | Muckter |
| 6,527,776 B1 | 3/2003 | Michelson |
| 6,565,569 B1 | 5/2003 | Assaker et al. |
| 6,575,975 B2 | 6/2003 | Brace et al. |
| D479,331 S | 9/2003 | Pike et al. |
| 6,623,486 B1 | 9/2003 | Weaver et al. |
| 6,669,701 B2 | 12/2003 | Steiner et al. |
| 6,719,759 B2 | 4/2004 | Wagner et al. |
| 6,730,091 B1 | 5/2004 | Pfefferle et al. |
| 6,893,443 B2 | 5/2005 | Frigg et al. |
| 6,955,677 B2 | 10/2005 | Dahners |
| 6,974,461 B1 | 12/2005 | Wolter |
| 7,044,953 B2 | 5/2006 | Capanni |
| 7,128,744 B2 | 10/2006 | Weaver et al. |
| 7,179,260 B2 | 2/2007 | Gerlach et al. |
| 7,309,340 B2 | 12/2007 | Fallin et al. |
| 7,338,491 B2 | 3/2008 | Baker et al. |
| 7,341,589 B2 | 3/2008 | Weaver et al. |
| 7,354,441 B2 | 4/2008 | Frigg |
| 7,537,596 B2 | 5/2009 | Jensen |
| 7,637,928 B2 | 12/2009 | Fernandez |
| 7,695,502 B2 | 4/2010 | Orbay et al. |
| 7,776,916 B2 | 8/2010 | Freeman et al. |
| 8,075,561 B2 | 12/2011 | Wolter |
| 8,118,846 B2 | 2/2012 | Leither et al. |
| 8,343,196 B2 | 1/2013 | Schneider |
| 8,574,268 B2 | 11/2013 | Chan et al. |
| 8,758,346 B2 | 6/2014 | Koay et al. |
| 8,845,698 B2 | 9/2014 | Schneider et al. |
| 8,852,245 B2 | 10/2014 | Schneider et al. |
| 8,876,873 B2 | 11/2014 | Schneider et al. |
| 2002/0156474 A1 | 10/2002 | Wack et al. |
| 2004/0073218 A1 | 4/2004 | Dahners |
| 2004/0260306 A1 | 12/2004 | Fallin et al. |
| 2005/0015089 A1 | 1/2005 | Young et al. |

(56) References Cited

U.S. PATENT DOCUMENTS

| | | |
|---|---|---|
| 2005/0107796 A1 | 5/2005 | Gerlach et al. |
| 2005/0165400 A1 | 7/2005 | Fernandez |
| 2005/0261688 A1 | 11/2005 | Grady et al. |
| 2006/0004361 A1 | 1/2006 | Hayeck et al. |
| 2006/0217722 A1 | 9/2006 | Dutoit et al. |
| 2006/0235400 A1 | 10/2006 | Schneider |
| 2007/0016205 A1 | 1/2007 | Beutter et al. |
| 2007/0088360 A1 | 4/2007 | Orbay et al. |
| 2007/0162016 A1 | 7/2007 | Matityahu |
| 2007/0206244 A1 | 9/2007 | Kobayashi |
| 2007/0260244 A1 | 11/2007 | Wolter |
| 2008/0140130 A1 | 6/2008 | Chan et al. |
| 2008/0208259 A1 | 8/2008 | Gilbert et al. |
| 2008/0234749 A1 | 9/2008 | Forstein |
| 2008/0300637 A1 | 12/2008 | Austin et al. |
| 2009/0018557 A1 | 1/2009 | Pisharodi |
| 2009/0018588 A1 | 1/2009 | Eckhof et al. |
| 2009/0076553 A1 | 3/2009 | Wolter |
| 2009/0076554 A1 | 3/2009 | Huebner et al. |
| 2009/0118768 A1 | 5/2009 | Sixto et al. |
| 2009/0143824 A1 | 6/2009 | Austin et al. |
| 2009/0143825 A1 | 6/2009 | Graham et al. |
| 2009/0292318 A1 | 11/2009 | White et al. |
| 2009/0312803 A1 | 12/2009 | Austin et al. |
| 2010/0016858 A1 | 1/2010 | Michel |
| 2010/0030277 A1 | 2/2010 | Haidukewych et al. |
| 2010/0057086 A1 | 3/2010 | Price et al. |
| 2010/0076496 A1 | 3/2010 | Fernandez |
| 2010/0094357 A1 | 4/2010 | Wallenstein et al. |
| 2010/0100134 A1 | 4/2010 | Mocanu |
| 2010/0137919 A1 | 6/2010 | Wolter |
| 2010/0274296 A1 | 10/2010 | Appenzeller et al. |
| 2010/0312286 A1 | 12/2010 | Dell'Oca |
| 2011/0224671 A1 | 9/2011 | Koay et al. |
| 2014/0180345 A1 | 6/2014 | Chan et al. |

FOREIGN PATENT DOCUMENTS

| | | |
|---|---|---|
| CH | 611147 | 5/1979 |
| CH | 672245 | 11/1989 |
| CH | 675531 | 10/1990 |
| DE | 3442004 | 4/1986 |
| DE | 4341980 | 6/1995 |
| DE | 4343117 | 6/1995 |
| DE | 4438264 | 3/1996 |
| DE | 19629011 | 1/1998 |
| DE | 9321544 | 10/1999 |
| DE | 19832513 | 2/2000 |
| DE | 20309361 | 9/2003 |
| DE | 20317651 | 3/2004 |
| DE | 10-2005-042766 | 1/2007 |
| EP | 0053999 | 6/1982 |
| EP | 158030 | 10/1985 |
| EP | 0207884 | 1/1987 |
| EP | 241914 | 10/1987 |
| EP | 0360139 | 3/1990 |
| EP | 0410309 | 1/1991 |
| EP | 0266146 | 12/1992 |
| EP | 0515828 | 12/1992 |
| EP | 0530585 | 3/1993 |
| EP | 0848600 | 6/1998 |
| EP | 1468655 | 10/2004 |
| EP | 1604619 | 12/2005 |
| EP | 1658015 | 5/2006 |
| EP | 1712197 | 10/2006 |
| EP | 1741397 | 1/2007 |
| EP | 1767160 | 3/2007 |
| FR | 742618 | 3/1933 |
| FR | 2233973 | 1/1975 |
| FR | 2405062 | 5/1979 |
| FR | 2405705 | 5/1979 |
| FR | 2405706 | 5/1979 |
| FR | 2496429 | 6/1982 |
| FR | 2674118 | 9/1992 |
| GB | 997733 | 7/1965 |
| GB | 1237405 | 6/1971 |
| GB | 1250413 | 10/1971 |
| GB | 1312189 | 4/1973 |
| GB | 1385398 | 2/1975 |
| GB | 1575194 | 9/1980 |
| JP | H11-512004 | 10/1999 |
| JP | 11299804 | 11/1999 |
| JP | 2001-525701 | 12/2001 |
| JP | 2001-525702 | 12/2001 |
| JP | 2002-232185 | 8/2002 |
| JP | 2002-542875 | 12/2002 |
| JP | 2003-509107 | 3/2003 |
| SU | 1037911 | 8/1883 |
| SU | 1279626 | 12/1986 |
| WO | WO 87/00419 | 1/1987 |
| WO | WO 87/06982 | 11/1987 |
| WO | WO 88/03781 | 6/1988 |
| WO | WO 96/29948 | 10/1996 |
| WO | WO 97/09000 | 3/1997 |
| WO | WO 98/51226 | 11/1998 |
| WO | WO 00/53110 | 9/2000 |
| WO | WO 00/53111 | 9/2000 |
| WO | WO 00/66012 | 11/2000 |
| WO | WO 01/19267 | 3/2001 |
| WO | WO 01/54601 | 8/2001 |
| WO | WO 02/096309 | 12/2002 |
| WO | WO 2004/089233 | 10/2004 |
| WO | WO 2005/018472 | 3/2005 |
| WO | WO 2007/014279 | 2/2007 |
| WO | WO 2007/108734 | 9/2007 |
| WO | WO 2009/023666 | 2/2009 |
| WO | WO 2009/058969 | 5/2009 |
| WO | WO 2011/032140 | 3/2011 |

OTHER PUBLICATIONS

"Multiple Offerings of Plates, Screws and Pegs", Small Bone Innovations, Inc., Dec. 2009, 3 pages.

ACE Symmetry, "Curves in All the Right Places", 1996, 3 pages.

ACE Symmetry™ Titanium Upper Extremity Plates, ACE Medical Company, 1996, 2 pages.

European Patent Application No. 12006606: Extended European Search Report dated Jan. 21, 2013, 8 pages.

European Patent Application No. 12006615; Extended European Search Report dated Jan. 21, 2013, 7 pages.

European Patent Application No. 12006617: Extended European Search Report dated Jan. 21, 2013, 8 pages.

International Search Report for International Application No. PCT/CH0300577 dated Apr. 28, 2004, German Language version.

International Search Report for International Application No. PCT/CH03/00577 dated Apr. 28, 2004, English language translation of the German language version.

Stryker, "VariAx Distal Radius: Locking Plate System", www.osteosynthesis.stryker.com, 2006, 12 pages.

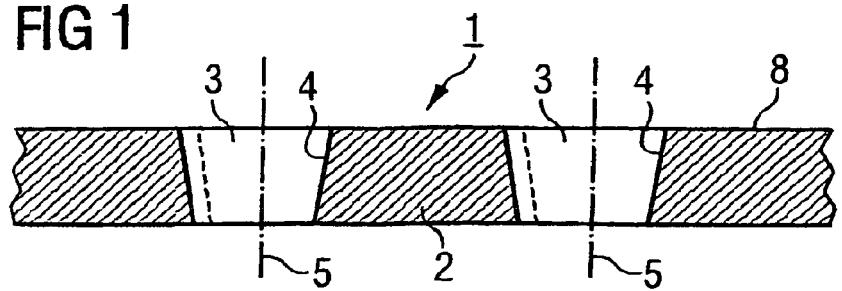
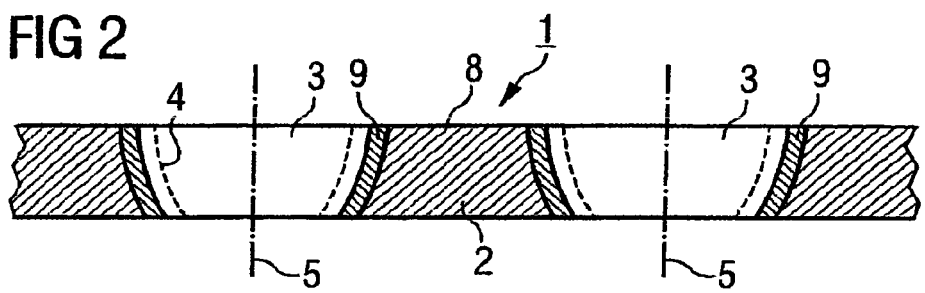
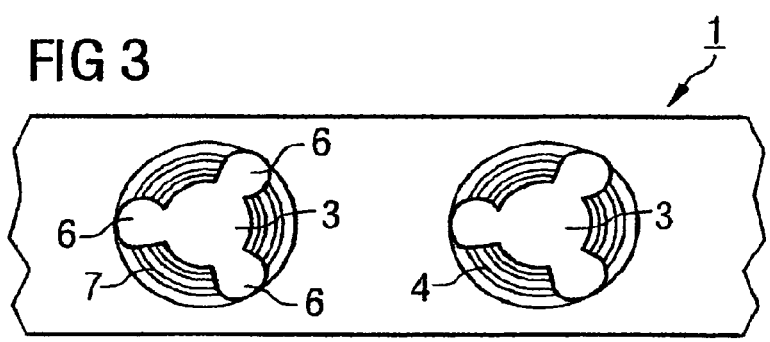
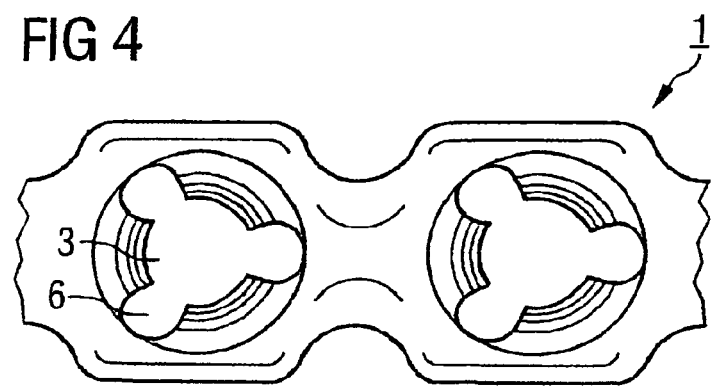

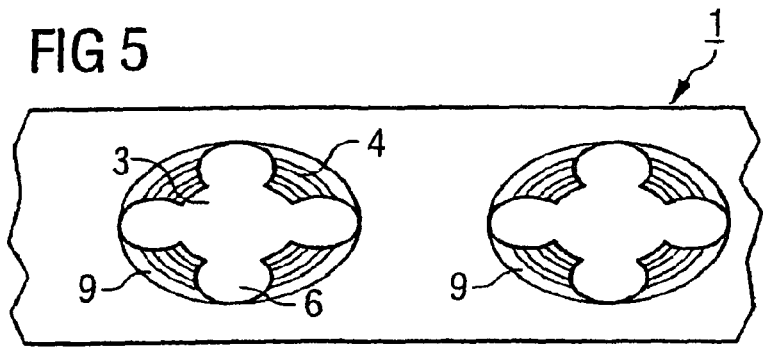
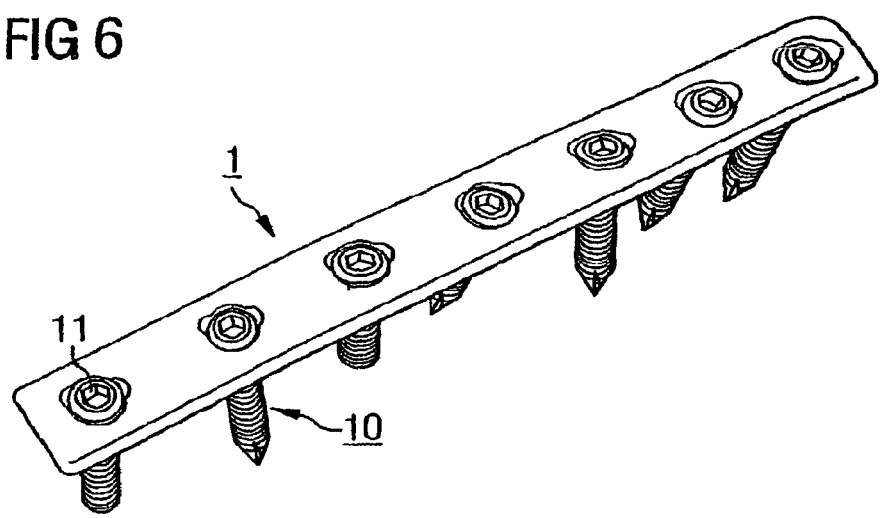
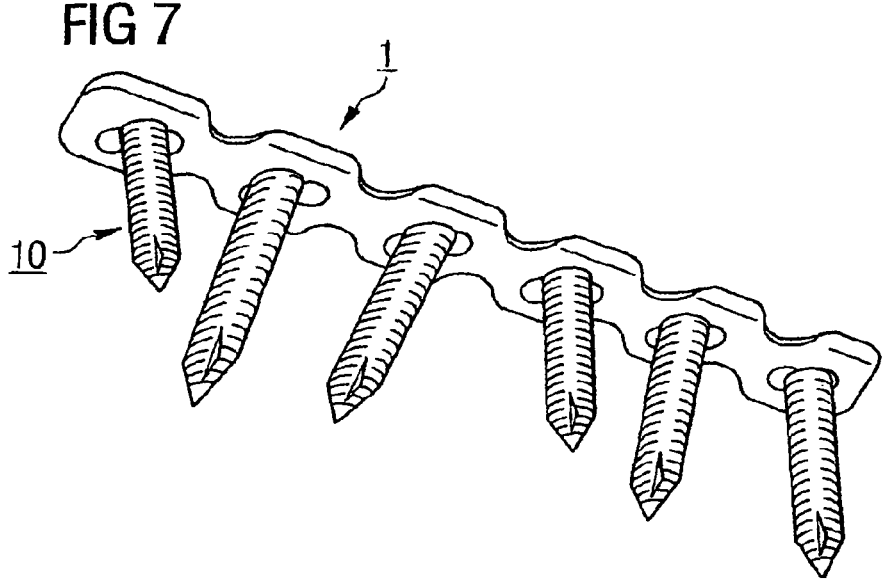

BONE PLATE

CROSS REFERENCE TO RELATED APPLICATIONS

This application is a continuation of U.S. patent application Ser. No. 13/795,596, filed Mar. 12, 2013, now U.S. Pat. No. 8,876,873, issued on Nov. 4, 2014, which is a continuation of U.S. patent application Ser. No. 13/713,626, filed Dec. 13, 2012, now U.S. Pat. No. 8,845,698, issued Sep. 30, 2014, which is a continuation of U.S. patent application Ser. No. 11/361,942, filed Feb. 24, 2006, now U.S. Pat. No. 8,343,196, issued on Jan. 1, 2013, which is a continuation of International Patent Application No. PCT/CH2003/000577, filed Aug. 26, 2003, the entire contents of which are expressly incorporated herein by reference thereto.

FIELD OF THE INVENTION

The invention relates to a bone plate for use in repairing bone fractures.

BACKGROUND OF THE INVENTION

Bone plates are known in the art and may be indicated for the entire skeleton. Particularly significant are, however, the usual large and small fragment indications for surgically treating bone breakages.

From DE-A 198 32 513 a bone plate of the generic type is known. In the case of this known device, the angular alignment of the bone screws relative to the bone plate and their angularly stable fixing is achieved by a ring arranged between the head of the screw and the hole in the plate. A disadvantage of this construction is, on the one hand, the more expensive manufacture with an additional component (ring) and the danger that the tiny ring will fall out or be pushed out from the hole in the plate, thus making the device unusable, and, on the other hand, the more expensive OP technique because the axis of the ring has to be correspondingly aligned before inserting the screw.

The present invention seeks to remedy this problem. The object of the invention is to produce a bone plate, without the need for additional components, that can accommodate conventional locking capscrews in an angularly and axially stable manner.

SUMMARY OF THE INVENTION

The invention achieves this objective with a bone plate having an upper surface, a lower surface, and at least one hole extending from the upper surface to the lower surface, the at least one hole having a central hole axis and an internal jacket surface. The internal jacket surface includes N recesses extending radially away from the central axis, where N≥3. The internal jacket surface may also include surface projections on at least a portion of the internal jacket surface.

The advantage achieved by the invention is essentially that as a result of the bone plate according to the invention a bone screw can be introduced at an angle that is different from the specified axis of the hole (usually at right angles to the plane of the bone plate) and secured in this position, without significantly sacrificing the stability, as is the case in known devices.

By virtue of the at least three recesses in the internal jacket surface of the holes in the plate, centralizing bearing surfaces are produced for the capscrew, even when the bone screw is inclined, and the bearing surfaces result in an even distribution of the load. In the case of bone screws with a threaded head and holes in the plate with an inner thread, when the screw is inclined, the threaded head can "jump over" the pitches of the thread in the hole of the plate interrupted by the recesses, without "cutting through" them.

A further advantage of the bone plate according to the invention is the possibility to use the at least three recesses in the hole in the plate to guide drilling bushings or guide bushings, by which the bone screws can be guided during their insertion. In this case the drilling bushings or guide bushings no longer need to be screwed into the holes in the plate (as is the case in the state-of-the-art), but due to the recesses need only to be inserted into the holes in the plate, resulting in a simple manner in the centre and direction of the axis of the hole. All that is required for this purpose is that the tips of the cannulated drilling bushings or guide bushings need to have the negative geometry of the holes in the plate, without any thread or other, similarly acting, structures. A snap-in mechanism may possibly be used in conjunction.

In one particular embodiment, the internal jacket surface of the hole in the plate is provided with a three-dimensional structure, which serves the purpose of guiding of a correspondingly structured capscrew. The three-dimensional structure is macroscopic and preferably comprises partial or complete pitches of a thread, ribs or protuberations. The internal jacket surface may be a multi-start thread.

The geometry of the surface of the N "locking leg", formed by the N recesses, is advantageously constructed to facilitate compatibility with the bone screw to be introduced. This can be in the form of a classic helical thread, a thread-like shape with or without pitch or also only a certain number of grooves or ribs, or also a quasi-thread with or without pitch. The number of grooves or ribs is preferably always odd (e.g. 3, 5, 7 or 9).

The internal jacket surface can have a concave, preferably spherical, tapered or ellipsoidal shape. This shape facilitates the insertion of a bone screw in such a manner that at the first contact of the bone screw with the internal jacket surface the bone screw is automatically pulled into the hole in the plate, without exerting prior a compression force on the bone via the bone plate, as is partly the case with devices known in the art.

In the case of a further development, at least one of the holes in the plate is constructed as an oblong hole.

The N recesses are arranged at a distance of 360°/N relative to the central axis. The recesses preferably have a peripheral expansion of at least 1° and a maximum of 119°. At the same time the N recesses divide the internal jacket surface into N sections of the jacket surface.

In the case of a particular embodiment the recesses extend exclusively within the internal jacket surface. In the case of another embodiment, the recesses extend radially away from the axis of the hole past the internal jacket surface.

The recesses may extend cylindrically or tapered from the upper side to the underside. The advantage of this is, that the recesses can be used for the fixing of a drilling bushing for pre-drilling or for the insertion of the Kirschner wires. Thus the drilling bushing no longer has to be screwed into the hole in the plate, only to be inserted without damaging the bearing area for the screw.

The recesses can extend from the upper side to the underside over the entire height of the bone plate.

The bone plate can be made from steel or titanium or also from a plastic material. In the case of plastic plates from polyacryl etherketone (PEAK) or polyether etherketone (PEEK) with an elongation at break of 40-70% and a modulus of elasticity of 3000-6000 N/mm² are preferred. However, polysulphon, having an elongation at break of 80-120% and a modulus of elasticity of 2000-3500 N/mm² may also be used. Furthermore, liquid crystal polymer (LCP) having an elongation at break of 1.5-2.5% and a modulus of elasticity of 5000-20000 N/mm² may be suitable. Finally, polyoxymethylene (POM) with an elongation at break of 10-50% and a modulus of elasticity of 2000-3500 N/mm² and polyphenylene sulphide (PPS) having an elongation at break of 0.2-1.0% and a modulus of elasticity of 12000-20000 N/mm² may be used.

Bone plates from plastic material may be reinforced with metal, plastic or carbon fibres.

Various bone screws can be used with the bone plates. For example, those having a convex, preferably spherical or tapered head portion. The head portion of the bone screws may also have a three-dimensional structure. In the case of a special embodiment the head portion of the bone screw is made from a material that is harder than the internal jacket surface of the bone plate. The internal jacket surface of the bone plate and the head portion of the bone screw have preferably matching threads.

In the case of a plastic plate, the holes in the plate may be executed as metallic thread inserts. Conversely, in the case of a metal bone plate the holes in the plate are executed as polymer thread inserts.

BRIEF DESCRIPTION OF THE DRAWINGS

The invention and developments of the invention are explained in detail based on the partly schematic illustrations of several embodiments in the figures, wherein:

FIG. 1 shows a longitudinal section through a bone plate with tapered holes in the plate;

FIG. 2 shows a longitudinal section through a bone plate with spherical holes in the plate;

FIG. 3 shows a top view of a bone plate with three recesses in the internal jacket surface of the holes in the plate;

FIG. 4 shows a variation of the bone plate according to FIG. 3 with larger recesses in the internal jacket surface of the holes in the plate;

FIG. 5 shows a top view of a bone plate with thread inserts with four recesses in the internal jacket surface of the elliptic holes in the plate;

FIG. 6 shows a perspective view of a bone plate according to FIG. 1 from above with the bone screws inserted;

FIG. 7 shows a perspective view of a bone plate according to FIG. 1 from below with the bone screws inserted;

DETAILED DESCRIPTION OF THE PREFERRED EMBODIMENTS

Figure 8:
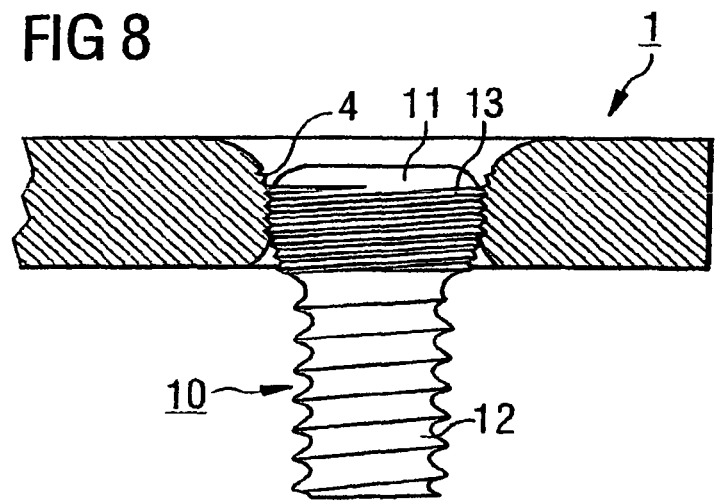
FIG. 8 shows a longitudinal section through a bone plate with a bone screw inserted without angular misalignment.

The bone plate 1 illustrated in FIGS. 1 and 3 has an underside 2 on the side of the bone, an upper side 8 and a plurality of holes 3 in the plate connecting the underside 2 with the upper side 8, the holes having a central hole axis 5. The holes 3 in the plate have an internal jacket surface 4 that tapers towards the underside 2. Furthermore, the internal jacket surface 4 has three recesses 6 which extend radially away from the hole axis 5 of the hole at a uniform distance of 120° from one another. Their peripheral expansion is approximately 40° and they extend exclusively within the internal jacket surface 4. The recesses 6 extend tapered over the entire height of the bone plate 1 from the upper side 8 to the underside 2. In addition, the internal jacket surface 4 is provided with a three-dimensional structure 7 in the form of a thread.

FIG. 4 illustrates a variation of the execution according to FIG. 3, wherein the recesses extend radially away from the axis of the hole past the internal jacket surface.

FIGS. 2 and 5 illustrate a further alternative embodiment, wherein the holes 3 in the plate are constructed as oblong holes. The bone plate is made basically from a plastic material (PEEK) with embedded metallic thread inserts 9 from titanium, forming the holes 3 in the plate. In the case of this embodiment the holes 3 in the plate have four recesses 6, which extend radially away from the axis 5 of the hole past the internal jacket surface 4. The internal jacket surface 4 is divided into four sections of the jacket surface. The recesses extend tapered over the entire height of the bone plate 1 from the upper side 8 to the underside 2. In addition, the internal jacket surface 4 is provided with a three-dimensional structure 7 in the form of a multi-start thread. As far as material is concerned, this embodiment may also be inverted, whereby the bone plate is basically made from metal (titanium) and the embedded therein thread inserts 9 are made from plastic material (PEEK), forming the holes 3 in the plate.

FIG. 6 illustrates the bone plate according to FIG. 1, with bone screws 10 inserted from above, the head portions 11 of which are spherical. FIG. 7 shows the same bone plate 1 from below.

In FIG. 8, a bone plate 1 is illustrated with bone screws 10 inserted therein without angular misalignment. The internal jacket surface 4 of the hole of the bone plate 1 and the head portion 11 of the bone screw 10 have matching threads 13.

Figure 9:
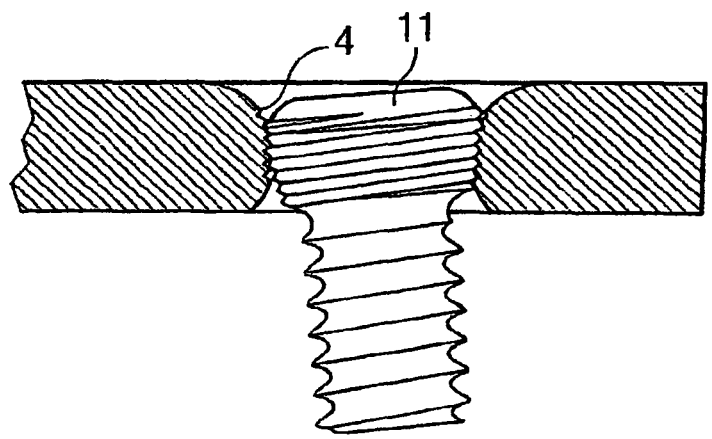
FIG. 9 shows a longitudinal section through a bone plate with a bone screw inserted with angular misalignment.

FIG. 9 illustrates the same variation as FIG. 8, while the bone screw 10 is angularly misaligned.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed:

1. A bone plate system comprising:
   a bone screw having a threaded head; and
   a bone plate defining a lower surface configured to face an underlying bone, an upper surface opposite the lower surface and configured to face away from the underlying bone, the bone plate further including:
   a first portion positioned between the upper surface and the lower surface;
   a second portion positioned between the first portion and the upper surface, such that the first and second portions cooperate to define a portion of a hole that extends from the upper surface to the lower surface along a central hole axis;
   a first projection and a second projection that each extends from the first portion toward the central hole axis, the first projection being spaced from the second projection circumferentially about the central hole axis by a gap that extends circumferentially from the first projection to the second projection, wherein the bone screw is configured to be inserted into the hole;
   wherein 1) the second portion is devoid of projections that are configured to threadedly mate with the threaded head of the bone screw when the bone screw is inserted in the hole, 2) the bone plate defines a line that extends from the upper surface, along the second portion and the first portion, toward the lower surface at a location circumferentially between the first projection and the second projection, such that the line does not pass through any projections that are configured to threadedly mate with the threaded head of the bone screw when the bone screw is inserted into the hole, and 3) the central hole axis lies within a plane and an entirety of the line lies within the plane.

2. The bone plate system of claim 1, wherein the bone plate includes an inner surface that extends between the upper surface and the lower surface, the inner surface including the first portion and the second portion, and the line extends along the inner surface from the upper surface to the lower surface.

3. The bone plate system of claim 1, wherein both the first projection and the second projection are configured to mate with the threaded head of the bone screw when the bone screw is inserted into the hole.

4. The bone plate system of claim 3, wherein the bone screw is elongate along a screw axis, both the first projection and the second projection are configured to mate with the threaded head of the bone screw when the bone screw is inserted into the hole such that the screw axis is at a first angle with respect to the central hole axis, and both the first projection and the second projection are configured to mate with the threaded head of the bone screw when the bone screw is inserted into the hole such that the screw axis is at a second angle with respect to the central hole axis, the second angle being different than the first angle.

5. The bone plate system of claim 4, wherein the bone plate comprises a column of projections that includes the first projection and a third projection that extends from the first portion of the inner surface toward the central hole axis, the first projection positioned closer to the upper surface than the third projection is positioned to the upper surface and the third projection positioned closer to the lower surface than the first projection is positioned to the lower surface.

6. The bone plate system of claim 5, wherein the column of projections is a first column of projections, the bone plate further including a second column of projections that includes the second projection and a fourth projection that extends from the first portion of the inner surface toward the central hole axis, the second projection positioned closer to the upper surface than the fourth projection is positioned to the upper surface and the second projection positioned closer to the lower surface than the fourth projection is positioned to the lower surface.

7. The bone plate system of claim 6, wherein the gap extends between the upper surface and the lower surface such that the third projection is spaced from the fourth projection circumferentially about the central hole axis by the gap.

8. The bone plate system of claim 7, wherein the head portion of the bone screw comprises a first material, the bone plate comprises a second material, and there is a hardness differential between the first material and the second material.

9. The bone plate system of claim 8, wherein the first portion and the second portion each comprises the second material.

10. The bone plate system of claim 8, wherein the first projection and the second projection each comprises the second material.

11. The bone plate system of claim 8, wherein the first material is harder than the second material.

12. The bone plate system of claim 6, wherein the second portion extends from the first column of projections to the upper surface.

13. The bone plate system of claim 12, wherein the inner surface further includes a third portion positioned between the first portion and the lower surface, and the third portion is devoid of projections.

14. The bone plate system of claim 13, wherein the third portion extends from the first column of projections to the lower surface.

15. The bone plate system of claim 1, wherein a cross-sectional dimension of the hole measured along a straight line that intersects the second portion and the central hole axis is greater than a cross-sectional dimension of the hole measured along a straight line that intersects the first portion and the central hole axis.

16. The bone plate system of claim 6, wherein the first column of projections includes a first set of projections and a second set of projections, the first set of projections are configured to mate with the threads of the head portion when the bone screw is inserted into the hole such that the screw axis is at a first angle with respect to the central hole axis, and the second set of projections are configured to mate with the threads of the head portion when the bone screw is inserted into the hole such that the screw axis is at a second angle with respect to the central hole axis, the second angle being different than the first angle, and at least some of the first column of projections included in the first set of projections are also included in the second set of projections.

17. The bone plate system of claim 1, wherein the line is a straight line.

18. The bone plate system of claim 1, wherein the bone screw is a first bone screw, the threaded head is a first threaded head, the bone plate is a first bone plate, the lower surface is a first lower surface, the upper surface is a first upper surface, the hole is a first hole, the central hole axis is a first central hole axis, the gap is a first gap, the line is a first line, and the plane is a first plane, the system further comprising:
    a second bone screw having a second threaded head; and
    a second bone plate defining a second lower surface configured to face an underlying bone, a second upper surface opposite the second lower surface and configured to face away from the underlying bone, the second bone plate further including:
        a third portion positioned between the second upper surface and the second lower surface;
        a fourth portion positioned between the third portion and the second upper surface, such that the third and fourth portions cooperate to define a second hole that extends from the second upper surface to the second lower surface along a second central hole axis;
        a third projection and a fourth projection that each extends from the third portion toward the second central hole axis, the third projection being spaced from the fourth projection circumferentially about the second central hole axis by a second gap that extends circumferentially from the third projection to the fourth projection, wherein the second bone screw is configured to be inserted into the second hole;
        wherein 1) the fourth portion is devoid of projections that are configured to threadedly mate with the second threaded head of the second bone screw when the second bone screw is inserted in the second hole, 2) the second bone plate defines a second line that extends from the second upper surface, along the fourth portion and the third portion, to the second lower surface at a location circumferentially between the third projection and the fourth projection, such that the second line does not pass through any projections that are configured to threadedly mate with the second threaded head of the second bone screw when the second bone screw is inserted into the second hole, and 3) the second central hole axis lies within a second plane and an entirety of the second line lies within the second plane.

19. The bone plate system of claim 18, wherein an outer periphery of the first bone plate defines a first shape, an outer periphery of the second bone plate defines a second shape, and the first shape is different than the second shape.

20. The bone plate system of claim 18, wherein the first line is a straight line and the second line is a straight line.

21. A bone plate system comprising:
a bone screw elongate along a central screw axis, the bone screw having a threaded head; and
a bone plate including a lower surface, an upper surface opposite the lower surface along a direction, and an inner surface that extends between the upper surface and the lower surface such that the inner surface defines a hole that extends from the upper surface to the lower surface along a central hole axis, the inner surface including a first portion positioned between the upper surface and the lower surface, the inner surface further including a second portion positioned between the first portion and the upper surface, the bone plate further including a column of projections having a first projection and a second projection of the first portion of the inner surface, the first projection being spaced from the second projection along the direction, wherein 1) the second portion of the inner surface is devoid of projections that are configured to threadedly mate with the threaded head of the bone screw when the bone screw is inserted in the hole, 2) the bone plate is devoid of any projections that intersect a line that extends along the inner surface from the upper surface toward the lower surface, and 3) the central hole axis and an entirety of the line lie within a common plane;
wherein both the first projection and the second projection are configured to mate with the threaded head of the bone screw when the bone screw is inserted into the hole such that the screw axis is at a first angle with respect to the central hole axis, and both the first projection and the second projection are configured to mate with the threaded head of the bone screw when the bone screw is inserted into the hole such that the screw axis is at a second angle with respect to the central hole axis, the second angle being different than the first angle.

22. The bone plate system of claim 21, wherein the column of projections is a first column of projections, the bone plate further including a second column of projections that includes a third projection and a fourth projection that each extends from the first portion of the inner surface toward the central hole axis, the third projection being spaced from the fourth projection along the direction.

23. The bone plate system of claim 22, wherein the bone plate defines a gap that extends between the upper surface and the lower surface such that the first projection and the third projection are radially spaced apart about the central hole axis by the gap.

24. The bone plate system of claim 23, wherein the threaded head of the bone screw comprises a first material, the bone plate comprises a second material, and there is a hardness differential between the first material and the second material.

25. The bone plate system of claim 24, wherein the inner surface comprises the second material.

26. The bone plate system of claim 24, wherein the column of projections comprises the second material.

27. The bone plate system of claim 24, wherein the first material is harder than the second material.

28. The bone plate system of claim 22, wherein the second portion extends from the first column of projections to the upper surface.

29. The bone plate system of claim 28, wherein the lower surface is configured to face bone.

30. The bone plate system of claim 29, wherein the inner surface further includes a third portion positioned between the first portion and the lower surface, and the third portion is devoid of projections.

31. The bone plate system of claim 30, wherein the third portion extends from the first column of projections to the lower surface.

32. The bone plate system of claim 21, wherein a cross-sectional dimension of the hole measured along a straight line that intersects the second portion and the central hole axis is greater than a cross-sectional dimension of the hole measured along a straight line that intersects the first portion and the central hole axis.

33. The bone plate system of claim 22, wherein the first column of projections includes a first set of projections and a second set of projections, the first set of projections are configured to mate with the threads of the head portion when the bone screw is inserted into the hole such that the screw axis is at a first angle with respect to the central hole axis, and the second set of projections are configured to mate with the threads of the head portion when the bone screw is inserted into the hole such that the screw axis is at a second angle with respect to the central hole axis, the second angle being different than the first angle, and at least some of the first column of projections included in the first set of projections are also included in the second set of projections.

34. The bone plate system of claim 21, wherein the line is a straight line.

35. The bone plate system of claim 21, wherein the bone screw is a first bone screw, the central screw axis is a first central screw axis, the threaded head is a first threaded head, the bone plate is a first bone plate, the lower surface is a first lower surface, the upper surface is a first upper surface, the direction is a first direction, the inner surface is a first inner surface, the hole is a first hole, the central hole axis is a first central hole axis, the column of projections is a first column of projections, the line is a first line, and the plane is a first plane, the system further comprising:
a second bone screw elongate along second a central screw axis, the second bone screw having a second threaded head; and
a second bone plate including a second lower surface, a second upper surface opposite the second lower surface along a second direction, and a second inner surface that extends between the second upper surface and the second lower surface such that the second inner surface defines a second hole that extends from the second upper surface to the second lower surface along a second central hole axis, the second inner surface including a third portion positioned between the second upper surface and the second lower surface, the second inner surface further including a fourth portion positioned between the third portion and the second upper surface, the second bone plate further including a second column of projections having a third projection and a fourth projection that each extends from the third portion of the second inner surface toward the second central hole axis, the third projection being spaced from the fourth projection along the second direction, wherein 1) the fourth portion of the second inner surface is devoid of projections, 2) the second bone plate is devoid of any projections that intersect a second line that extends along the second inner surface from the second upper surface to the second lower surface, and 3) the second central hole axis lies within a second plane and an entirety of the second line lies within the second plane;

wherein both the third projection and the fourth projection are configured to mate with the second threaded head of the second bone screw when the second bone screw is inserted into the second hole such that the second screw axis is at a third angle with respect to the second central hole axis, and both the third projection and the fourth projection are configured to mate with the second threaded head of the second bone screw when the second bone screw is inserted into the second hole such that the second screw axis is at a fourth angle with respect to the second central hole axis, the fourth angle being different than the third angle.

36. The bone plate system of claim 35, wherein an outer periphery of the first bone plate defines a first shape, an outer periphery of the second bone plate defines a second shape, and the first shape is different than the second shape.

37. The bone plate system of claim 35, wherein the first line is a straight line and the second line is a straight line.

38. The bone plate system of claim 21, wherein prior to insertion of the bone screw, both the first projection and the second projection are configured to mate with the threaded head of the bone screw when: 1) the screw axis is at a first angle with respect to the central hole axis, and 2) the screw axis is at a second angle with respect to the central hole axis, the second angle being different than the first angle.

\* \* \* \* \*